(12) United States Patent
Georgeson et al.

(10) Patent No.: US 7,617,715 B2
(45) Date of Patent: Nov. 17, 2009

(54) REFERENCE STANDARD FOR ULTRASONIC MEASUREMENT OF POROSITY AND RELATED METHOD

(75) Inventors: Gary E. Georgeson, Federal Way, WA (US); Joseph Hafenrichter, Bellevue, WA (US); David A. Lilienthal, Kent, WA (US); James C. Kennedy, Renton, WA (US); Walter J. Harris, Kent, WA (US)

(73) Assignee: The Boeing Company, Chicago, IL (US)

( * ) Notice: Subject to any disclaimer, the term of this patent is extended or adjusted under 35 U.S.C. 154(b) by 321 days.

(21) Appl. No.: 11/643,112

(22) Filed: Dec. 21, 2006

(65) Prior Publication Data

US 2008/0148854 A1 Jun. 26, 2008

(51) Int. Cl.
*G01N 29/30* (2006.01)
*G01R 31/28* (2006.01)

(52) U.S. Cl. .......................... 73/1.86; 29/593
(58) Field of Classification Search ................. 73/1.03, 73/1.86, 599, 622, 1.84, 1.82; 29/593
See application file for complete search history.

(56) References Cited

U.S. PATENT DOCUMENTS

| | | | |
|---|---|---|---|
| 3,908,439 A | | 9/1975 | Peiak, et al. |
| 3,933,026 A | | 1/1976 | Ham |
| 4,156,123 A | | 5/1979 | Fischer et al. |
| 4,173,139 A | * | 11/1979 | Conn ......................... 73/1.84 |
| 4,266,154 A | | 5/1981 | Marshall |
| 4,393,987 A | | 7/1983 | Anderson et al. |
| 4,406,153 A | | 9/1983 | Ophir et al. |
| 4,445,360 A | * | 5/1984 | Treder, Jr. .................... 73/588 |
| 4,466,270 A | | 8/1984 | Kimura et al. |
| 4,566,330 A | | 1/1986 | Fujii et al. |
| 4,660,419 A | * | 4/1987 | Derkacs et al. ................. 73/622 |
| 4,674,334 A | | 6/1987 | Chimenti et al. |
| 4,704,892 A | * | 11/1987 | Tarnai ......................... 73/1.86 |
| 4,747,295 A | * | 5/1988 | Feist et al. .................... 73/1.86 |
| 5,054,310 A | | 10/1991 | Flynn |
| 5,127,268 A | | 7/1992 | Kline |
| 5,163,027 A | | 11/1992 | Miller et al. |
| 5,196,343 A | | 3/1993 | Zerhouni et al. |
| 5,238,556 A | | 8/1993 | Shirkhan |
| 5,312,755 A | | 5/1994 | Madsen et al. |
| 5,448,129 A | * | 9/1995 | Sumihara et al. ........ 310/323.11 |
| 5,637,175 A | | 6/1997 | Feygin et al. |
| 5,656,763 A | | 8/1997 | Flax |

(Continued)

FOREIGN PATENT DOCUMENTS

GB 2221991 A 2/1990

(Continued)

*Primary Examiner*—J M Saint Surin
(74) *Attorney, Agent, or Firm*—Tung & Associates

(57) ABSTRACT

Ultrasonic measurements of porosity in manufactured parts or materials are calibrated using reference standards in which parallel holes are drilled in the backside of a body of material. The holes simulate voids in a part which attenuate incident ultrasonic energy. The number, size and location of the holes determine the simulated level of porosity that may be used to calibrate an ultrasonic tester. Multiple reference standards representing different levels of porosity can be produced in the form of individual coupons, or in a single body having multiple groups of holes.

29 Claims, 7 Drawing Sheets

U.S. PATENT DOCUMENTS

| | | |
|---|---|---|
| 5,662,566 A | 9/1997 | Marxrieser et al. |
| 5,837,880 A | 11/1998 | Shakinovsky et al. |
| 6,238,343 B1 | 5/2001 | Madsen et al. |
| 6,405,583 B1 | 6/2002 | Shirakawabe et al. |
| 6,415,051 B1 | 7/2002 | Callari et al. |
| 6,415,644 B1 | 7/2002 | Rockwood et al. |
| 6,426,274 B1 | 7/2002 | Tayanaka |
| 6,649,516 B2 | 11/2003 | Asakawa et al. |
| 6,684,701 B2 | 2/2004 | Dubois et al. |
| 6,803,095 B1 | 10/2004 | Halladay et al. |
| 6,959,602 B2 | 11/2005 | Peterson et al. |
| 6,962,739 B1 | 11/2005 | Kim et al. |
| 7,076,992 B2 | 7/2006 | Greelish |
| 7,188,559 B1 | 3/2007 | Vecchio |
| 7,216,544 B2 | 5/2007 | Vaccaro et al. |
| 7,320,241 B2 | 1/2008 | Kollgaard et al. |
| 7,353,709 B2 | 4/2008 | Kruger et al. |
| 7,357,014 B2 | 4/2008 | Vaccaro et al. |
| 7,418,860 B2 | 9/2008 | Austerlitz, et al. |
| 7,424,818 B2 | 9/2008 | Vaccaro, et al, |
| 7,509,832 B2 | 3/2009 | Vaccaro et al. |
| 7,510,817 B2 | 3/2009 | Benoit et al. |
| 2006/0213250 A1 | 9/2006 | Vaccaro et al. |
| 2006/0234391 A1 | 10/2006 | Weiss et al. |
| 2006/0265679 A1 | 11/2006 | Scheffer et al. |
| 2007/0107520 A1 | 5/2007 | Vaccaro et al. |
| 2007/0125177 A1 | 6/2007 | Vaccaro et al. |
| 2008/0087093 A1 | 4/2008 | Engelbart et al. |
| 2008/0134749 A1 | 6/2008 | Engelbart et al. |
| 2008/0196475 A1 | 8/2008 | Engelbart et al. |

FOREIGN PATENT DOCUMENTS

| | | |
|---|---|---|
| JP | 08210953 A | 8/1996 |

* cited by examiner

REFERENCE STANDARD FOR ULTRASONIC MEASUREMENT OF POROSITY AND RELATED METHOD

BACKGROUND OF THE INVENTION

1. Technical Field

This invention generally relates to nondestructive testing and inspection techniques, and deals more particularly with a reference standard and related method used to calibrate ultrasonic measurements of porosity in manufactured parts, particularly those of composite materials.

2. Description of the Related Art

It is often useful to know the porosity of a manufactured part in order to determine its suitability for a particular application or whether it meets a product specification. Porosity is normally defined as the ratio of pores or voids in a part relative to the total volume occupied by the part.

Various technologies have been employed to determine the porosity of the part, including the use of ultrasonic sound in which a beam of ultrasonic energy is directed into the part whose porosity is to be measured. Any voids that may be present in the part attenuate the sound beam in proportion to the porosity of the part. The magnitude of the attenuated beam, which may either pass through the part or be reflected back through the transmission path, is measured to determine the porosity.

In order to accurately measure porosity, porosity reference standards must be used to determine whether the measured porosity is accurate. In the past, porosity reference standards were manufactured in which an attempt was made to produce voids in a reference standard part or block, so that the degree of porosity would be known. This approach was not only time consuming and expensive, but produced results that were not always uniform.

One of the areas in which measurements of porosity is useful is that of parts and structures made from composite materials, such as those used in the aerospace industry. Laminated plies of fiber reinforced polymers have wide spread use in commercial and military aircraft. During the manufacturing stages, multiple plies or layers of fiber reinforced materials are laid up, compacted and then cured to produce homogeneous, rigid structures. If the compaction of the plies is not uniform or inadequate compaction pressure is employed during the production process, voids within the layers may be left that may reduce the structural strength of the part or cause delamination over the service life of the part. Porosity measurement is also important when patching or repairing composite parts since voids can be left along the bondline between the new material of the patch and the old material of the structure.

Accordingly, there is a need for a reference standard used in the ultrasonic measurement of porosity of manufactured parts, particularly those made of composite materials, which is relatively inexpensive to produce and yields accurate, uniform and reproducible results. The present invention is directed toward satisfying this need.

BRIEF SUMMARY OF THE INVENTION

In accordance with one aspect of the invention, a method is provided for manufacturing a reference standard for calibrating readings produced by an ultrasonic tester used to measure porosity of a material. The method comprises the steps of providing a solid body formed of a material through which ultrasonic energy may be transmitted, and forming a plurality of holes partially through the body, each hole representing a discontinuity that attenuates the ultrasonic energy passing through the body.

In accordance with another aspect of the invention, a reference standard is provided for determining multiple degrees of porosity of one or more parts using ultrasonic energy. The reference standard comprises a body formed of a material through which ultrasonic energy may pass. The body has a plurality of groups of holes therein, the holes passing partially through the body and representing discontinuities that attenuate the ultrasonic energy passing through the body. Each of groups of holes represents a reference standard for determining one of the plurality of degrees of porosity.

According to still another aspect of the invention, a reference standard is provided for calibrating readings produced by an ultrasonic tester used to determine the porosity of a material, wherein voids in the material attenuate the ultrasonic energy emitted by the tester. The reference standard comprises a body formed of material through which ultrasonic energy may pass, and, a plurality of holes in the body. The holes pass partially through the body and represent discontinuities that attenuate the ultrasonic energy passing through the body. The holes preferably extend parallel to each other. A filler material may be used to partially fill each of the holes to prevent the intrusion of foreign substances into the holes. The body may be of unitary construction.

These and further features, aspects and advantages of the embodiments will become better understood with reference to the following illustrations, description and claims.

DETAILED DESCRIPTION OF THE INVENTION

Figure 1:
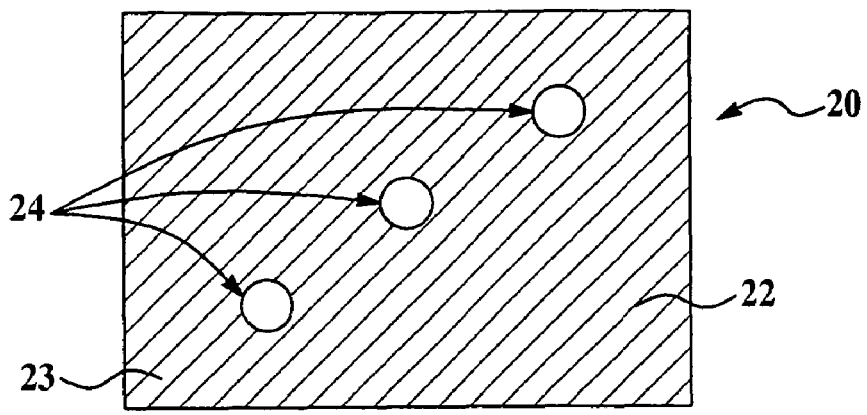
FIG. 1 is a bottom view of a reference standard for used in the ultrasonic measurement of porosity, according to the present invention.
Figure 2:
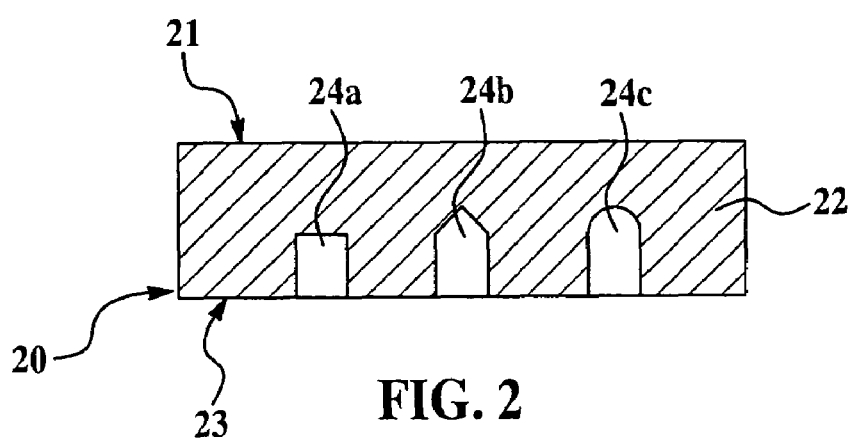
FIG. 2 is a side view of the reference standard shown in FIG. 1 and depicting three different hole profiles.
Figure 3:
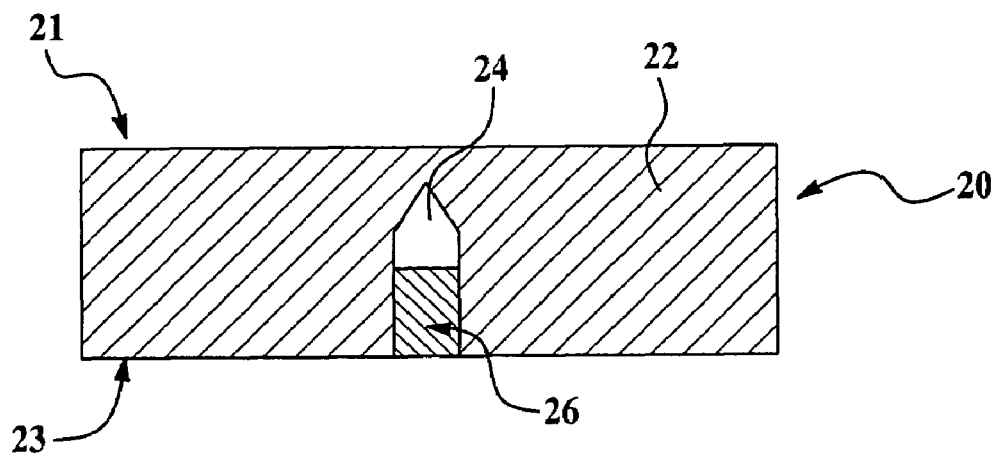
FIG. 3 is a side view of a reference standard in which a hole has been partially filled.

Referring first to FIGS. 1 and 2, the present invention relates to a reference standard 20 comprising a body 22 of suitable material that is used to calibrate equipment (not shown) for measuring the porosity of a part (not shown) using ultrasonic energy. The reference standard 20 can be used, for example, to perform pulse-echo ultrasonic inspection of composite patches and composite structures in general. The reference standard 20 simulates the ultrasonic pulse echo response to specific levels and depths of porosity. The standard 20 can be easily tailored and fabricated consistently and repeatably, at low cost.

The reference standard 20 may possess any of various shapes, but in the illustrated example comprises a rectangular shape having a uniform thickness throughout. The body 22 may comprise any of various materials that allow the transmission of ultrasonic energy. In one embodiment, the body 22 of the reference standard 20 may be formed from an acrylic material. In some cases, it may be desirable to employ material for the body 22 that is the same as that whose porosity is to be measured. Thus for example, when measuring a part formed from a carbon fiber reinforced composite polymer, it may be desirable to use the same material for the reference standard 20.

In accordance with the present invention, a series of holes 24 each having a circular cross section are formed in the body 22 of the reference standard 20. The holes 24 may be formed using any of various techniques, such as drilling, milling, EDM machining and other techniques. It may also be possible to use tooling features to form the holes by molding the body 22. The holes 24, which may sometimes be referred to herein as "drill holes" extend from the bottom surface 23 of the body 22 upwardly to a predetermined height. The drill holes 24 preferably extend parallel to each other, perpendicular to the top and bottom surfaces 21, 23 of the body 22, and parallel to the direction of travel of a later discussed beam of ultrasonic energy. As will be discussed below in more detail, the number, diameter and depth of the drill holes 24 will determine the apparent porosity of the reference standard 20, as measured by the ultrasonic measurement equipment. The bottoms of the drill holes 24 may possess any of various geometries, including those formed using common cutting tools such as drills and mills. In the illustration shown in FIG. 2, the end profiles of holes 24 reflect flat, pointed and rounded shapes, 24a, 24b and 24c respectively. It should be noted here that although holes 24 of circular cross section are shown in the illustrated embodiment, other forms of elongate channels may be employed that have a depth and bottom or end wall. Also, the channels may have cross sectional shapes other than circular.

In some applications, it may be desirable that the drill holes 24 remain free from intrusion of debris or liquids so as to not alter the ultrasonic response of the reference standard 20. Accordingly, the holes 24 may be at least partially filled with a filler material 26, such as foam. In most cases, it is desirable to use a filler material 26 that is essentially transparent to the ultrasonic energy used during the measurement process so as not to alter the response of the ultrasonic energy to the holes 24.

Figure 4:
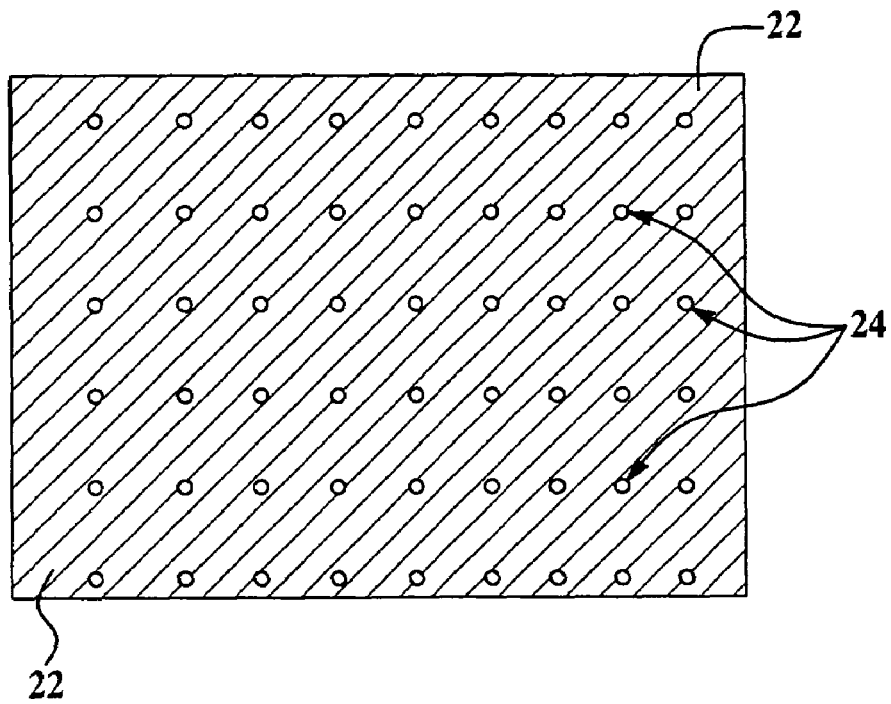
FIG. 4 is a bottom view of a reference standard having a uniform grid layout of holes.
Figure 5:
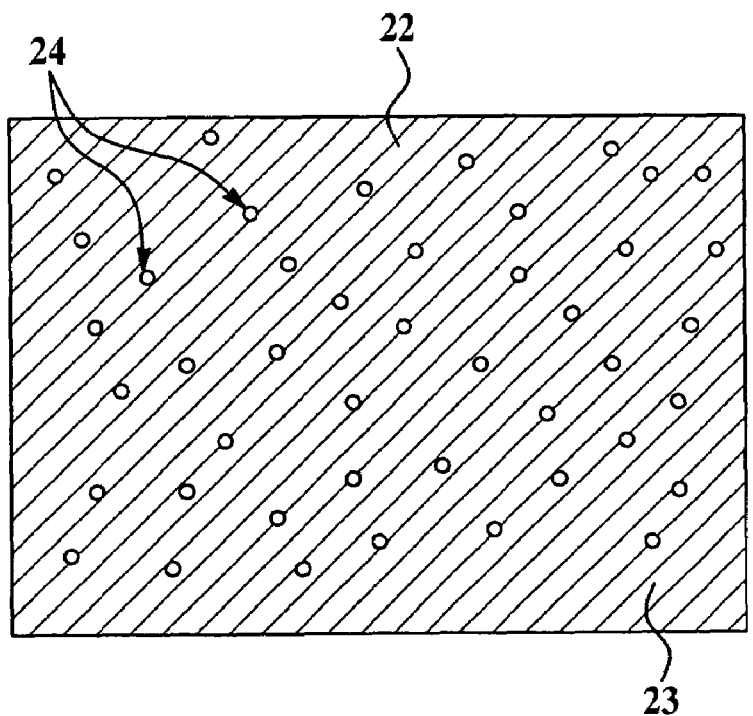
FIG. 5 is a bottom view of a reference standard having a random hole layout pattern.

The drill holes 24 may be arranged in a uniform pattern such as the uniform grid pattern shown in FIG. 4, or may be randomly arranged, as shown in FIG. 5. In the case of either layout, a programmed machining center can be used to precisely duplicate the hole pattern for each of a plurality of reference standards 20.

Figure 6:
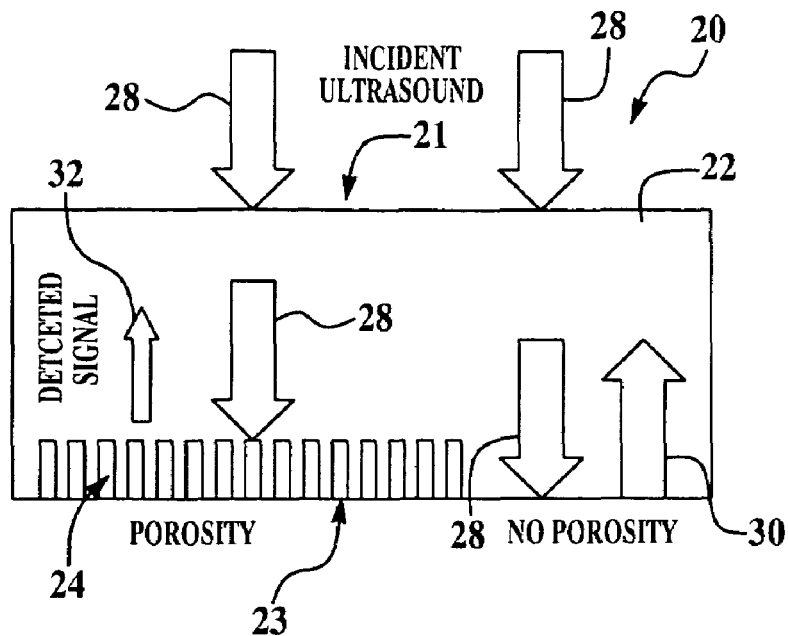
FIG. 6 is a side view of a reference standard according to the present invention, illustrating the use of pulse-echo (PE) ultrasonic measurement.

FIG. 6 illustrates the principles of using the reference standard 20 of the present invention to establish ultrasonic measurements of porosity. Ultrasonic sound energy 28 is directed from a source (not shown) perpendicular to and through the upper surface 21 of the reference standard 20. The ultrasonic energy 28 typically has a frequency of between 0.1 MHz and 25 MHz. The ultrasonic sound beam passes into the body of the reference standard 20. As shown on the right side of FIG. 6, in the absence of drill holes 24 simulating the effect of voids in a part, the ultrasonic beam is reflected from the bottom 23 of the standard 20, resulting in a reflected beam 30 that is picked up by a transducer (not shown) at virtually the same strength at which it entered the reference standard 20. However, as shown on the left side of FIG. 6, when the incident beam 28 encounters the drill holes 24, a portion of the ultrasonic energy is scattered, thereby attenuating the magnitude of the incident beam 28. The beam passes upwardly as a reflected but attenuated signal 32 whose amplitude is measurably less than the original incident beam $28_{[GEGI]}$.

As previously indicated, the number, size and location of the drill holes 24 determines the amount of beam attenuation that is achieved. For a given ultrasonic test system, a specimen with a known level of "real porosity" may be used to calibrate the reference standard 20, enabling the standard to be stamped with a label indicating the percent porosity for that reference standard. As previously noted, the longitudinal axes of the drill holes 24 are arranged parallel both to each other and the direction of the incident beam 28. This drill hole 24 orientation presents discontinuities to the principle sound beam that is suggestive of the shape of porosity itself. The dependence of the ultrasonic attenuation on changes in the sound beam shape and size may closely track the attenuation changes that would occur with "real porosity".

Although the drill holes 24 may be formed in the side of the material forming the reference standard 20, the vertical orientation of the drill holes 24 shown in the drawings provides a number of benefits, including those discussed immediately above. Generally, drill holes 24 that are arranged parallel to the direction of the ultrasonic beam 28 produce the desired signal attenuation using a shallower depth, consequently the drilled holes 24 do not have to be as deep as holes that are arranged to extend perpendicular to the direction of the sound beam 28.

In applications where it is desired to measure the porosity of a graphite (carbon) composite part, it may be desirable to use graphite material as the body 22. Using a graphite or graphite composite as a reference standard, for a given thickness, the attenuation of a drill hole free standard is near the same as the attenuation of a porosity free standard. In the case of graphite composite materials, attenuation levels have been achieved over a range sufficient to represent porosity levels from 0% to 8%.

Figure 7:
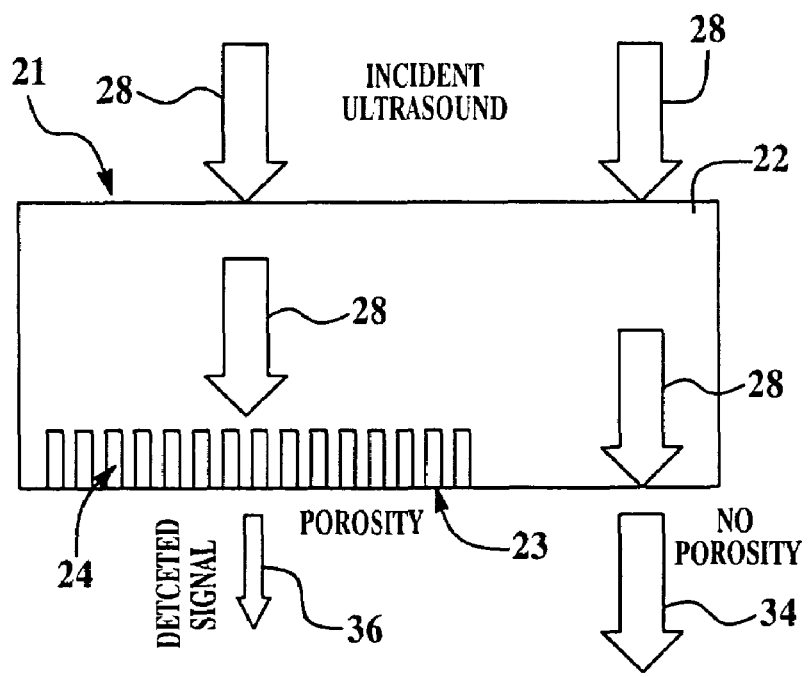
FIG. 7 is a view similar to FIG. 6 but illustrating the use of ultrasonic measurement in a through transmission (TTU) mode.

FIG. 7 illustrates the use of a reference standard in the through transmission (TTU) mode for detecting and quantifying the percent by volume of porosity in materials such as composite materials. The incident ultrasonic sound beam 28 passes through the reference standard 20, and in the absence of porosity, passes through the bottom of the standard 20 to emerge as an un-attenuated signal 34. However, the drill holes 24 result in some scattering of the incident sound beam 28, thereby attenuating the signal 36 as it emerges from the bottom 23 of the standard 22.

Figure 8:
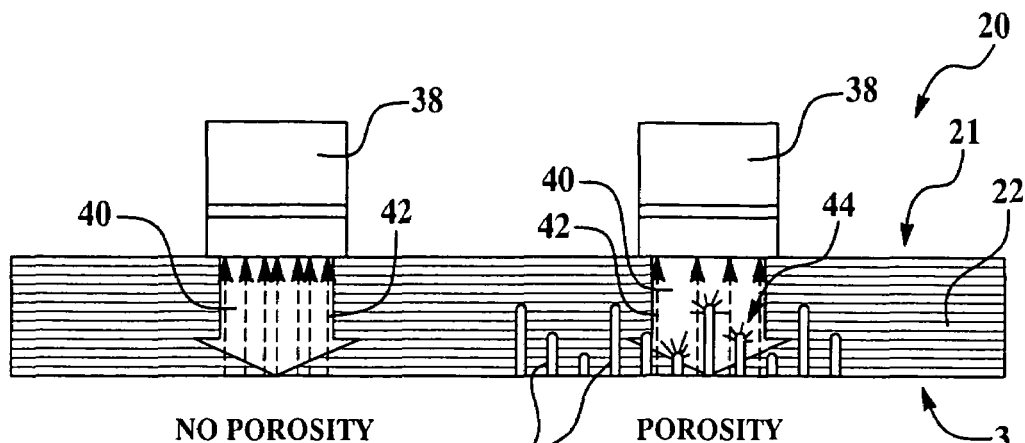
FIG. 8 is a side view of a reference standard showing the interaction of drill holes with incident ultrasound energy.

FIG. 8 illustrates the use of a pulse echo (PE) type ultrasonic tester 38 which is moved across the upper surface 21 of a reference standard 20. The tester 38 directs an ultrasonic sound beam 40 downwardly through a reference standard 20, having drill holes 24 of varying depth. The incident sound beam 40 encounters the upper ends of the drill holes 24, resulting in scattering of some of the energy so that the reflected signal 42 is attenuated in strength.

Figure 9:
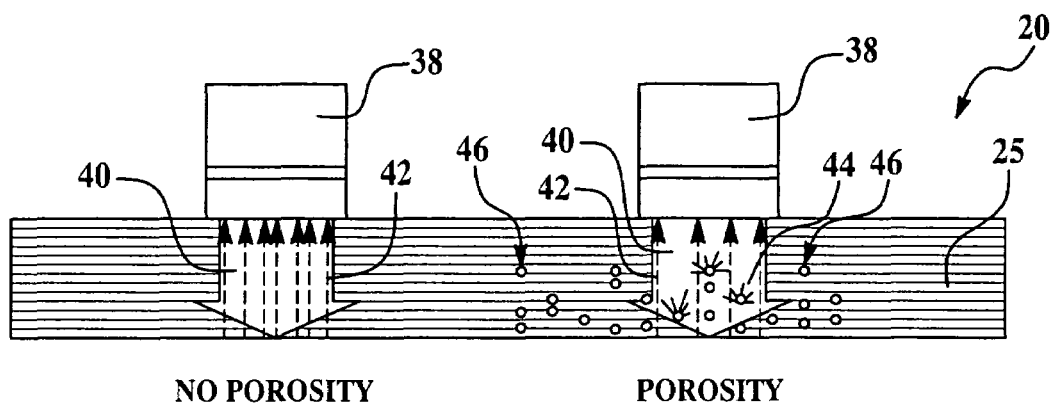
FIG. 9 is a view similar to FIG. 8 but showing the reflected ultrasound energy during measurement of actual porosity in a part.

FIG. 9 shows the use of the tester 38 on a part of other material 25 whose porosity is to be tested. As was the case in the illustration shown in FIG. 8, the incident energy beam 40 encounters pores or voids 46 in the material 25 which cause partial dispersion of the incident beam 40. The reflected sound energy 42, which is picked up in a transducer (which is nominally the same transducer as the sender for pulse-echo inspection) forming part of the tester, is an attenuated signal whose strength is related to the percentage of porosity in the material 25. With this actual signal strength known, the tester 38 is then passed over the surface of a series of reference standards 20 which are calibrated to provide a return signal strength indicative of a specific percent porosity. Using a plurality of these reference standards 20, the operator can determine which specific reference standard yields a signal strength approximately equal to that obtained in the part or material being tested. The use of drill holes 24 of varying depths as shown in FIG. 8 is effective in establishing a reference standard to determine the porosity of a part in which the voids or pores forming the porosity are found at various depths.

Figure 10:
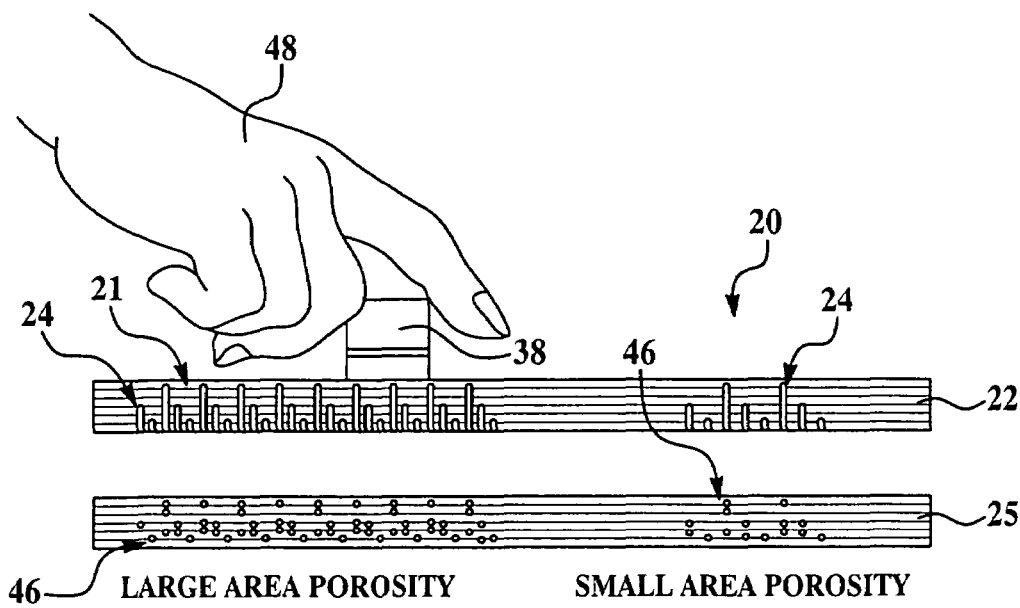
FIG. 10 is a side view of a reference standard and a part illustrating the difference between measuring large area porosity and small area porosity.

FIG. 10 shows how an operator's hand 48 moves an ultrasonic tester 38 over the surfaces of a reference standard 22 and a part 25 to detect large or small areas of porosity. FIG. 10 shows that patterns of drill holes 24 formed in a reference standard 20 may be used to test smaller or larger regions of porosity.

Figure 11:
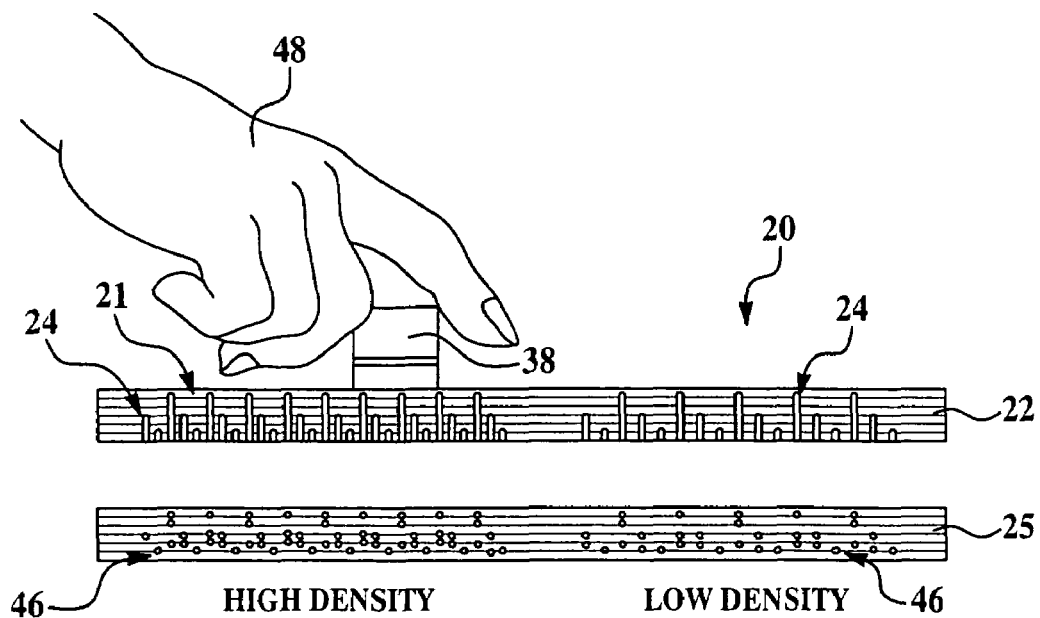
FIG. 11 is a view similar to FIG. 10 but illustrating the difference in measuring high density and low density porosity.

FIG. 11 shows that a reference standard 20 may include drill holes 24 of higher or lower densities to determine porosity where the voids producing porosity may have a high or low density.

Figure 12:
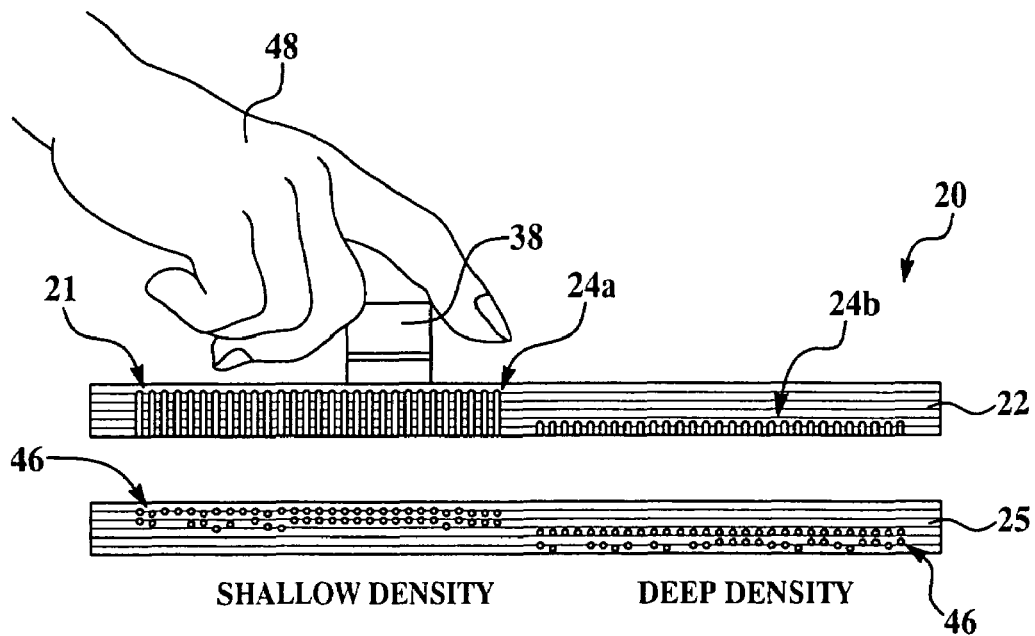
FIG. 12 is similar to FIG. 10, but showing the difference in measuring shallow porosity and deep porosity.

FIG. 12 illustrates a reference standard 20 that has stepped sets of drill holes 24, respectively designated as 24a and 24b. This reference standard 20 is useful in determining the porosity of the part in which the voids are stepped from a shallow porosity to a deep porosity. An example of this type of stepped, porosity variation is a scarf joint formed of composite materials where, for example, a defect in a composite structural member has been patched using composite material that is joined to the existing material by a scarf joint, in which the joint represents a sharp transition in porosity.

Figure 13:
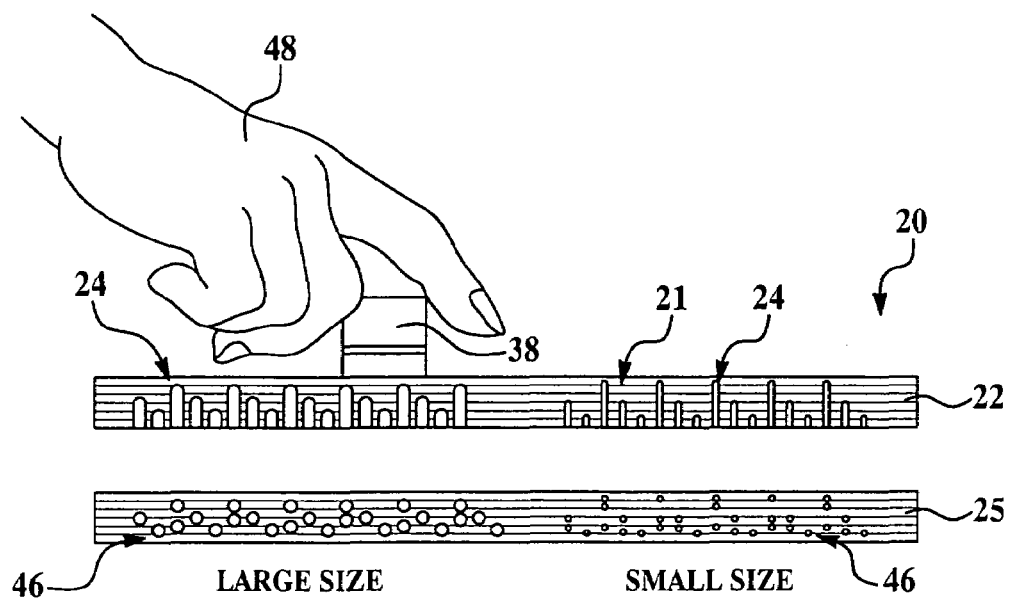
FIG. 13 is similar to FIG. 10 but showing the difference in measuring porosity in which the voids are large and porosity in which the voids are small.

FIG. 13 illustrates a reference standard in which the size of the drill holes 24 is selected so as to mimic voids in a part which have either a larger size or a smaller size.

Figure 14:
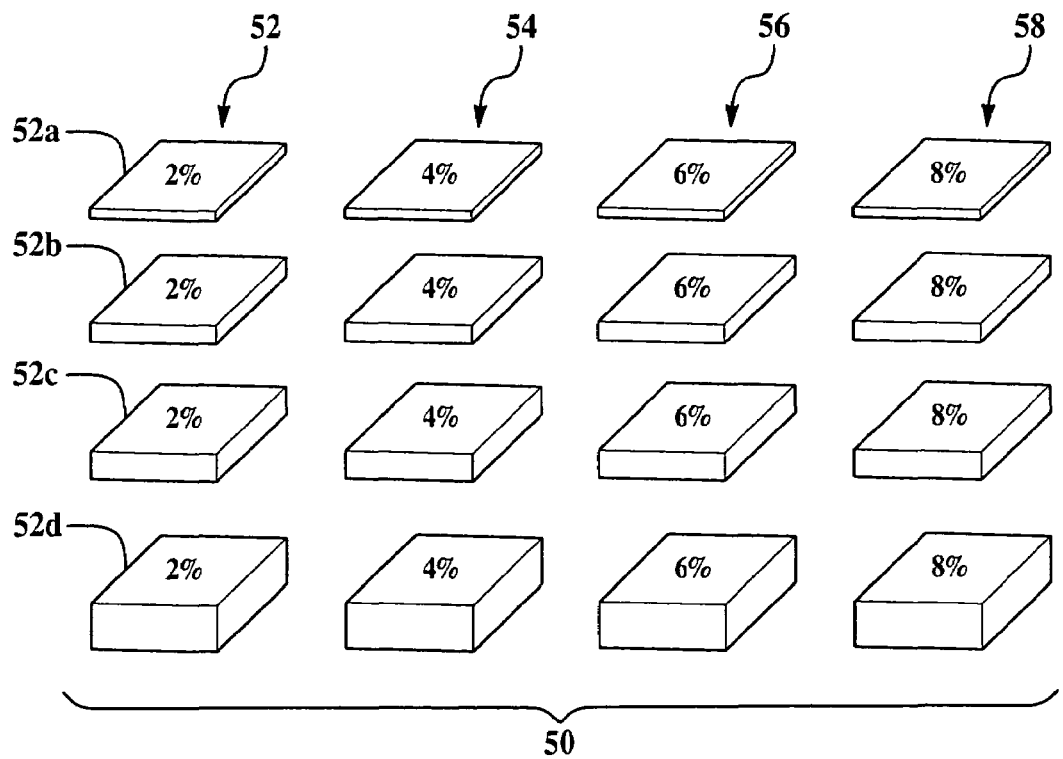
FIG. 14 is a perspective view of a family of reference standards in the form of individual coupons.

FIG. 14 illustrates use of a plurality of reference standards in the form of coupons that are used to determine percent porosities in different thicknesses of parts. Thus, a family 50 of reference standards comprises four groups 52, 54, 56, 58 which are respectively used to determine porosities of 2%, 4%, 6%, and 8%. Each of the groups 52-58 contains four reference standards of differing thicknesses. For example, group 52 includes four individual standards 52a, 52b, 52c, 52d used in determining 2% porosity for each of four different part thicknesses. The drill holes (not shown) in reference standards shown in FIG. 14 are sized and located such that each standard yields a test reading (percentage porosity) when used on a part of a corresponding thickness.

Figure 15:
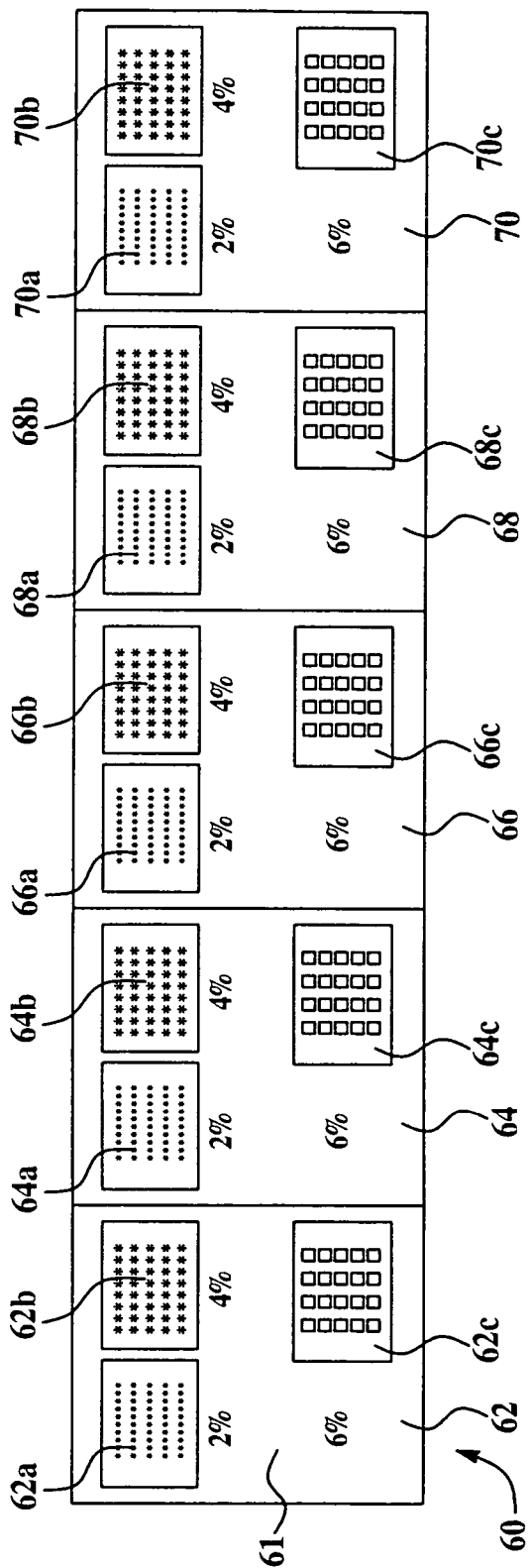
FIG. 15 is a plan view of a composite reference standard used for multiple porosities, for multiple material thicknesses.
Figure 16:
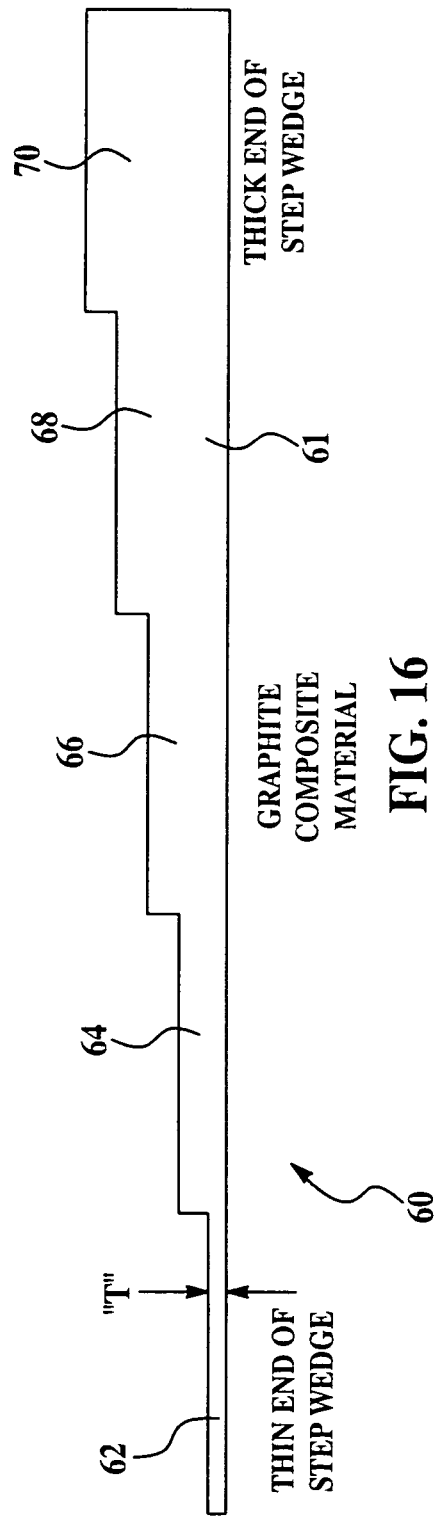
FIG. 16 is a side elevation view of the composite reference standard shown in FIG. 15.

FIGS. 15 and 16 illustrate a composite reference standard 60 that may be used to determine multiple percentage porosities for each of several thicknesses. The composite standard 60 a single body 61 having five sections 62-70 of progressively greater thicknesses "T". The body may be of unitary construction made from a single material, or multiple body portions joined together. Each section 62-70 includes three individual reference standards, 62a-62c, 64a-64c, 66a-66c, 68a-68c, and 70a-70c. Each of the individual reference standards, e.g. 62a-62c is provided with sets of drill holes that are different in size, quantity or placement so as to reflect a test value of the percentage porosity for a particular part thickness. Thus, a single composite reference standard 60 may be used in lieu of the family 50 of individual reference standards shown in FIG. 14 to allow an operator to determine the percentage porosity of multiple parts of various thicknesses.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of manufacturing a reference standard for calibrating readings produced by an ultrasonic tester used to measure porosity of a material, comprising the steps of:
   (A) providing a body of material through which ultrasonic energy may be transmitted; and,
   (B) forming a plurality of holes partially through the body, each of said holes extending from a common surface of said body, each hole representing a discontinuity that attenuates the ultrasonic energy passing through the body, said holes arranged so that two or more of said holes have the same depth to simultaneously receive ultrasonic energy to simulate porosity.

2. The method of claim 1, wherein step (A) includes selecting a material for the body that approximates ultrasonic transmission qualities of the material from which the part is formed.

3. The method of claim 1, wherein step (B) is performed by machining the holes into the bottom of the body.

4. The method of claim 1, wherein step (B) is performed by machining the holes into the side of the body.

5. The method of claim 3, wherein the machining is performed by drilling parallel holes in the body.

6. The method of claim 1, further comprising the step of:
   (C) introducing a filler material into the holes to prevent the intrusion of debris or fluids into the holes.

7. The method of claim 1, further comprising the step of:
   (C) selecting a characteristic of the holes that approximately produces an attenuation matching the attenuation produced by voids in the material.

8. The method of claim 7, wherein the characteristic includes at least one of:
   the cross sectional area of each of the holes, the depth of each of the holes, and the two dimensional layout of the holes.

9. The method of claim 1, wherein step (B) includes:
   forming the holes in a plurality of groups, the groups respectively corresponding to a plurality of levels of porosity.

10. A reference standard for determining multiple degrees of porosity of one or more parts using ultrasonic energy, comprising:
    a body formed of a material through which ultrasonic energy may pass, the body having a plurality of groups of holes therein, the holes passing partially through the body and representing discontinuities that attenuate the ultrasonic energy passing through the body, each of said groups of holes representing a reference standard for determining one of the plurality of degrees of porosity;

wherein each of said groups of holes extends from a common surface of said body and are arranged so that two or more of said holes in a respective group have the same depth to simultaneously receive ultrasonic energy to simulate porosity.

11. The reference standard of claim 10, wherein the body is of unitary construction.

12. The reference standard of claim 10, wherein the body includes a plurality of sections respectively containing the groups of holes, wherein the sections have different thicknesses respectively related to the thicknesses of parts whose porosity may be measured.

13. The reference standard of claim 10, wherein the body is formed of a carbon composite material.

14. The reference standard of claim 10, wherein the holes extend parallel to each other and parallel to the direction of the ultrasonic energy passing through the body.

15. The reference standard of claim 10, wherein each of the holes has a rounded hole bottom, said rounded hole bottom having a concave curvature extending longitudinally to said hole.

16. The reference standard of claim 10, wherein the body has top and bottom flat surfaces, and the top and bottom surfaces extend parallel to each other.

17. The reference standard of claim 10, further comprising a filler material at least partially filling the holes to prevent the intrusion of debris or fluids into the holes.

18. The reference standard of claim 10, wherein the body is generally wedge shape in cross section and includes a plurality of steps of progressive greater thickness, each of the steps including one of the groups of holes therein.

19. The reference standard of claim 10, wherein the holes in each of the groups include a characteristic that approximately produces an attenuation matching the attenuation produced by voids in the part.

20. The reference standard of claim 19, wherein the characteristic includes at least one of:

the cross sectional area of each of the holes, the depth of each of the holes, and the two dimensional layout of the holes.

21. A reference standard for calibrating readings produced by an ultrasonic tester used to determine the porosity of a material, wherein voids in the material attenuate the ultrasonic energy beam emitted by the tester, comprising:

a body formed of material through which ultrasonic energy beam may pass; and, a plurality of holes in the body, the holes passing partially through the body and representing discontinuities that attenuate the ultrasonic energy passing through the body;

wherein each of said holes in a respective group extends from a common surface of said body and said holes are arranged so that two or more of said holes have the same depth to simultaneously receive ultrasonic energy to simulate porosity.

22. The reference standard of claim 21, wherein the holes extend parallel to each other and generally parallel to the direction of travel of the ultrasonic energy beam.

23. The reference standard of claim 21, wherein each of the holes includes a hole bottom having a curved cross sectional shape, said curved cross sectional shape having a concave curvature extending longitudinally to said hole.

24. The reference standard of claim 21, further comprising a filler material partially filling each of the holes to prevent the intrusion of foreign substances into the holes.

25. The reference standard of claim 21, wherein the body is of unitary construction.

26. The reference standard of claim 21, wherein the body is formed of a carbon composite material.

27. The reference standard of claim 21, wherein the body has top and bottom flat surfaces, and the top and bottom surfaces extend parallel to each other.

28. The reference standard of claim 21, wherein the holes include a characteristic that approximately produces an attenuation matching the attenuation produced by voids in the material.

29. The reference standard of claim 28, wherein the characteristic includes at least one of:

the cross sectional area of each of the holes, the depth of each of the holes, and the two dimensional layout of the holes.

* * * * *